US006977272B2

(12) United States Patent
Wilkemeyer et al.

(10) Patent No.: US 6,977,272 B2
(45) Date of Patent: *Dec. 20, 2005

(54) METHOD FOR ANTAGONIZING INHIBITION EFFECTS OF ALCOHOL ON CELL ADHESION

(75) Inventors: Michael F. Wilkemeyer, Allston, MA (US); Michael E. Charness, Waban, MA (US)

(73) Assignees: President and Fellows of Harvard College, Cambridge, MA (US); The United States of America as represented by the United States Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/270,551

(22) Filed: Oct. 16, 2002

(65) Prior Publication Data

US 2004/0077731 A1 Apr. 22, 2004

(51) Int. Cl.[7] ........................ A61K 31/045; A61K 31/05
(52) U.S. Cl. ........................................ 514/724; 514/731
(58) Field of Search ................................ 514/724, 731, 514/729

(56) References Cited

U.S. PATENT DOCUMENTS

| | | | |
|---|---|---|---|
| 5,496,851 A | | 3/1996 | Grinnell |
| 6,169,071 B1 | | 1/2001 | Blaschuk et al. |
| 6,169,072 B1 | | 1/2001 | Jonczyk et al. |
| 6,359,015 B1 | * | 3/2002 | Charness et al. |

OTHER PUBLICATIONS

Fransen E, Lemmon V, Van Camp G. Vits L, Coucke P and Willems PJ (1995) CRASH Syndrome: Clinical Spectrum of Corpus Callosum Hypoplasia, Retardation, Adducted Thumbs, Spastic Paraparesis and Hydrocephalus Due to Mutations in One Single Gene, L1. [Review]*Eur. J. Hum. Genet.* 3:273–284.

Uyemura K, Asou H, Yazaki T and Takeda Y (1996) Cel-l–adhesion proteins of the immunoglobulin superfamily in the nervouse system. *Essays in Biochemistry.* 31:37–48.

Anders DL, Blevins T, Sutton G, Swope S, Chandler LJ and Woodward JJ (1999) Fyn tyrosine kinase reduces the ethanol inhibition of recombinant NR1/NR2A but not NR1/NR2B NMDA receptors expressed in HEK 293 cells. *J. Neurochem.* 72:1389–1393.

Bearer CF, Swick, AR, O'Riordan MA and Cheng G (1999) Ethanol inhibits L1–mediated neurite outgrowth in postnatal rat cerebellar granule cells. *J. Biol. Chem.* 274:13264–13270.

Beckstead MJ, Phelan R and Mihic SJ (2001) Antagonism of inhalant and volatile anesthetic enhancement of glycine receptor function. *J. Biol. Chem.* 276:24959–24964.

Charness ME, Querimit LA and Diamond I (1986) *J. Biol. Chem.* 261:3164–3169.

(Continued)

*Primary Examiner*—Phyllis G. Spivack
(74) *Attorney, Agent, or Firm*—Dinesh Agarwal, P.C.

(57) ABSTRACT

A method of antagonizing inhibition effects of alcohol on cell adhesion is disclosed comprising contacting a cell-adhesion molecule expressing cell with an effective amount of a compound, wherein the compound comprises an alcohol selected from the group consisting of 3-pentanol, 2-pentanol, cyclopentanol, 4-methyl-1-pentanol, 2-methyl-2-pentanol, and 2,6-diisopropylphenol.

3 Claims, 8 Drawing Sheets

OTHER PUBLICATIONS

Charness ME, Safran RM and Perides G (1994) Ethanol inhibits neural cell–cell adhesion. *J. Biol. Chem.* 269:9304–9309.

Charness ME, Simon RP and Greenberg DA (1989) Ethanol and the nervous system. *N. Engl. J. Med.* 321:442–454.

Chen S–Y, Wilkemeyer MF, Sulik KK and Charness ME (2001) Octanol antagonism of ethanol teratogenesis. *Faseb J.* 15(9):1649–1651.

Coe IR, Dohrman DP, Constantinescu A, Diamond I and Gordon AS (1996) Activation of cyclic AMP–dependent protein kinase reverses tolerance of a nucleoside transporter to ethanol. *J. Pharmacol. Exp. Ther.* 276:365–369.

Crossin KL and Krushel LA (2000) Cellular signalling by neural cell adhesion molecules of the immunoglobulin superfamily. *Developmental Dynamics* 218:260–279.

Demyanenko GP, Tsai AY and Maness PF (1999) Abnormalities in neuronal process extension, hippocampal development, and the ventriclar system of L1 knockout mice. *J. Neurosci.* 19:4907–4920.

Diamond I and Gordon AS (1997) Cellular and molecular neuroscience of alcoholism. *Physiol. Rev* 77:1–20.

Dwyer DS and Bradley RJ (2000) Chemical properties of alcohols and their protein binding sites. *Cell Mol. Life Sci.* 57:265–275.

Franks NP & Lieb WR (1984) Do general anaesthetics act by competitive binding to specific receptors? *Nature* 310:599–601.

Franks NP and Lieb WR (1994) Molecular and cellular mechanisms of general anaesthesia. *Nature* 367:607–614.

Fransen E, Dhooge R, Vancamp G, Verhoye M, Sijbers J, Reyniers E, Soriano P, Kamiguchi H, Willemsen R, Koekkoek SKE, Dezeeuw CI, Dedeyn PP, Vanderlinden A, Lemmon V, Kooy RF and Willems PJ (1998) L1 knockout mice show dilated ventricles, vermis hypoplasia and impaired exploration patterns. *Human Mol. Genet.* 7:999–1009.

Goldstein DB (1983) *Pharmacology of Alcohol.* Oxford, New York.

Harris RA (1999) Ethanol actions on multiple ion channels: which are important? *Alcohol Clin. Exp. Res.* 23:1563–1570.

Harris T, Shahidullah M, Ellingson JS and Covarrubias M (2000) General anesthetic action at an internal protein site involving the S4–S5 cytoplasmic loop of a neuronal K(+) channel. *J. Biol. Chem.* 275:4928–4936.

Hodge CW, Mehmert KK, Kelley SP, McMahon T, Haywood A, Olive MF, Wang D, Sanchez–Perez AM and Messing RO (1999) Supersensitivity to allosteric GABA(A) receptor modulators and alcohol in mice lacking PKCepsilon. *Nature Neuroscience* 2:997–1002.

Hundle B, McMahon T, Dadgar J. Chen CH, Mochly–Rosen D and Messing RO (1997) An inhibitory fragment derived from protein kinase Cepsilon prevents enhancement of nerve growth factor responses by ethanol and phorbol esters. *J. Biol. Chem.* 272:15028–15035.

Kamiguchi H and Lemmon V (1998) A neuronal form of the cell adhesion molecule L1 contains a tyrosine–based signal required for sorting to the axonal growth cone. *J. Neurosci.* 18:3749–3756.

Lewohl JM, Wilson WR, Mayfield RD, Brozowski SJ, Morrisett RA and Harris RA (1999) G–protein–coupled inwardly rectifying potassium channels are targets of alcohol action. *Nat. Neurosci.* 2:1084–1090.

Lovinger DM (1999) 5–HT3 receptors and the neural actions of alcohols: an increasingly exciting topic. *Neurochem. Int.* 35:125–130.

Lüthl A, Laurent J–P, Figurov A, Muller D and Schachner M (1994) Hippocampal long–term potentiation and neural cell adhesion molecules L1 and NCAM. *Nature* 372:777–779.

Mascia MP, Mihic SJ, Valenzuela CF, Schofield PR and Harris RA (1996) A single amino acid determines differences in ethanol actions on strychnine–sensitive glycine receptors. *Mol. Pharmacol.* 50:402–406.

Msacia MP, Trudell JR and Harris RA (2000) Specific binding sites for alcohols and anesthetics on ligand–gated ion channels. *Proc. Natl. Acad. Sci. U.S.A.* 97:9305–9310.

Mascia MP, Wick MJ, Martinez LD and Harris RA (1998) Enhancement of glycine receptor function by ethanol: role of phosphorylation. *Br. J. Pharmacol.* 125:263–270.

McCreery MJ and Hunt WA (1978) Physico–chemical correlates of alcohol intoxication. *Neuropharmacol.* 17:451–461.

McKenzie D, Franks NP and Lieb WR (1995) Actions of general anaesthetics on a neuronal nicotinic acetylcholine receptor in isolated identified neurones of *Lymnaea stagnalis*. *Br. J. Pharmacol.* 115:275–282.

Mihic SJ, Ye Q, Wick MJ, Koltchine VV, Krasowski MD, Finn SE, Mascia MP, Valenzuela CF, Hanson KK, Greenblatt EP, Harris RA and Harrison NL (1997) Sites of alcohol and volatile anaesthetic action on GABA(A) and glycine receptors [see comments]. *Nature* 389:385–389.

Minami K, Gereau RWt, Minami M. Heinemann SF and Harris RA (1998). Effects of ethanol and anesthetics on type 1 and 5 metabotropic glutamate receptors expressed in *Xenopus laevis* oocytes. *Mol. Pharmacol.* 53:148–156.

Miyakawa T, Yagi T, Kitazawa H, Yasuda M, Kawai N, Tsuboi K and Niki H (1997) Fyn–kinase as a determinant of ethanol sensitivity: relation to NMDA–receptor function [see comments]. *Science* 278:698–701.

Peoples RW, Li C and Weight FF (1996) Lipids vs protein theories of alcohol action in the nervous system. *Ann. Rev. Pharmacol. Toxicol.* 36: 185–201.

Perides G, Hu G, Rueger DC and Charness ME (1993) Osteogenic Protein–1 Regulates L1 and Neural Cell Adhesion Molecule Gene Expression in Neural Cells. *J. Biol. Chem.* 268:25197–25205.

Perides G, Safan RM, Downing LA and Charness ME (1991) Regulation of Neural Cell Adhesion Molecule and L1 by the Transforming Growth Factor–β Superfamily. *J. Biol. Chem.* 269:765–770.

Perides G, Safran RM, Rueger DC and Charness ME (1992) induction of the neural cell adhesion molecule and neuronal aggregation by osteogenic protein 1. *Proc. Natl. Acad. Sci.* (USA) 89:10326–10330.

Ramanathan R, Wilkemeyer MF, Mittal B, Perides G and Charness ME (1996) Ethanol inhibits cell–cell adhesion mediated by human L1. *J. Cell Biol.* 133:381–390.

Rose SP (1995) Glycoproteins and memory formation. *Behav. Brain Res.* 66:73–78.

Sanna E, Dildy–Mayfield JE and Harris RA (1994) Ethanol inhibits the function of 5–hydroxytryptamine type 1c and muscarinic M1 G protein–linked receptors in *Xenopus* oocytes expressing brain mRNA: role of protein kinase C. *Mol. Pharmacol.* 45:1004–1012.

Slater SJ, Cox KJ, Lombardi JV, Ho C, Kelly MB, Rubin E and Stubbs CD (1993) Inhibition of protein kinase C by alcohols and anaesthetics. *Nature* 364:82–84.

Solem M, McMahon T and Messing RO (1997) Protein kinase A regulates regulates inhibition of N– and P/Q–type calcium channels by ethanol in PC12 cells, *J. Pharmacol. Exp. Ther.* 282:1487–1495.

Uyemura K, Asou H, Yazaki T and Takeda Y (1996) *Essays Biochem.* 31:37–48.

Vallejo Y, Hortsch M and Dubreuil RR (1997) Ethanol Does Not Inhibit the Adhesive Activity of *Drosophila Neuroglian* or Human L1 in *Drosophila* S2 Tissue Culture Cells. *J. Biol. Chem.* 272:12244–7.

Wick MJ, Mihic SJ, Ueno S, Mascia MP, Trudell JR, Brozowski SJ, Ya Q. Harrison NL and Harris RA (1998) Mutations of gamma–aminobutyric acid and glycine receptors change alcohol cutoff: Evidence for an alcohol receptor? *Proc. Natl. Acad. Sci. (U.S.A.)* 95:6504–6509.

Wilkemeyer MF and Charness ME (1998) Characterization of alcohol–sensitive and insensitive fibroblast cell lines expressing human L1. *J. Neurochem.* 71:2382–2391.

Wilkemeyer, M.F., Menkari C.E., Charness, M.E., (Nov. 2002—available online Oct. 22, 2002) Novel Antagonists of Alcohol Inhibition of L1–Mediated Cell Adhesion: Multiple Mechanisms of Action. *Molecular Pharmacology* 62:1053–1060.

Wilkemeyer MF, Pajerski M and Charness ME (1999) Alcohol Inhibition of cell adhesion in BMP–treated NG108–15 cells. *Alcohol Clin. Exp. Res.* 23:1711–1720.

Wilkemeyer MF, Sebastian AB, Smith SA and Charness ME (2000) Antagonists of alcohol inhibition of cell adhesion. *Proc. Natl. Acad. Sci. (U.S.A.)* 97:3690–3695.

Wong EV, Kenwrick S, Willems P and Lemmon V (1995) Mutations In the cell adhesion molecule L1 cause mental retardation. *Trends Neurosci.* 18:168–172.

Ye Q, Koltchine VV, Mihic SJ, Mascia MP, Wick MJ, Finn SE, Harrison NL and Harris RA (1998) Enhancement of glycine receptor function by ethanol is inversely correlated with molecular volume at position alpha267. *J. Biol. Chem.* 273:3314–3319.

Zhou QL, Zhou Q and Forman SA (2000) The n–alcohol site in the nicotinic receptor pore is a hydrophobic patch. *Biochemistry* 39:14920–14926.

Zisch AH, Stallcup WB, Chong LD, Dahlinhuppe K, Voshol J, Schachner M and Pasquale EB (1997) Tyrosine phosphorylation of L1 family adhesion molecules—implication of the Eph Kinase Cek5. *J. Neurosci. Res.* 47:655–665.

Wilkemeyer, M.F., Couper, C.E., and Charness, M.E., Multiple Mechanisms for Antagonism of Alcohol Inhibition of Cell Adhesion, Alcoholism—Clinical and Experimental Research, May 2001, (RSA Abstract No. 401) vol. 25, No. 5 (2 pages).

Wilkemeyer, M.F., Smith, S.A., and Charness, M.E., Structure Activity Relation of Antagonists for Ethanol Inhibition of Cell Adhesion, Alcoholism—Clinical and Experimental Research, May 2000, p. 30A (RSA Abstract No. 144) vol. 24, No. 5 (2 pages).

\* cited by examiner

METHOD FOR ANTAGONIZING INHIBITION EFFECTS OF ALCOHOL ON CELL ADHESION

BACKGROUND OF THE INVENTION

The present invention is directed to inhibiting alcohol effects on cell adhesion, and more particularly to method and compound for antagonizing inhibition effects of alcohol on cell adhesion, and further to the use of alcohol inhibition antagonists in prophylaxis or treatment of toxic effects of alcohol.

Ethanol is a pleiotropic, weak central nervous system (CNS) drug (Charness et al., 1989). Ethanol potency is orders of magnitude less than that of other psychoactive drugs. This low potency indicates that the brain does not express a high-affinity ethanol receptor; rather, ethanol is believed to produce its CNS effects by interacting at millimolar concentrations with components of diverse neurotransmitter systems (Diamond and Gordon, 1997). For many years, the prevailing view was that ethanol modified synaptic activity by altering the biophysical properties of neuronal membranes, thereby disrupting indirectly the function of various membrane proteins (Goldstein, 1983). Recent research, however, suggests that ethanol interacts directly with small regions of selective neuronal proteins (Slater et al., 1993; Franks and Lieb, 1994; Harris, 1999).

The immunoglobulin neural cell adhesion molecule L1 is a multifunctional, transmembrane protein that binds to L1 molecules on adjacent cells and to selective proteins in the extracellular matrix, cell membrane, and cytoskeleton (Crossin and Krushel, 2000). L1 interactions control cell-cell and cell-matrix events that are essential for growth cone mobility, axon pathfinding, axon fasciculation, and neuronal migration. L1 binding also triggers a series of transmembrane signaling events, resulting in neurite outgrowth and changes in growth cone morphology. L1 is expressed in the developing nervous system, where it plays a critical role in CNS development (Fransen et al., 1995; Fransen et al., 1998; Demyanenko et al., 1999), and in the mature CNS, where it may be involved in learning and memory (Lüthi et al., 1994; Rose, 1995).

Mutations in the gene for L1 are associated with hydrocephalus, agenesis of the corpus callosum, cerebellar dysplasia and a variety of other brain malformations (Fransen et al., 1995). Because children with fetal alcohol syndrome have neuropathology similar to that of children with L1 mutations, we studied the effects of ethanol on L1-mediated cell-cell adhesion (Charness et al., 1994; Ramanathan et al., 1996). Clinically-relevant concentrations of ethanol inhibited L1-mediated cell adhesion in NG108-15 neuroblastoma×glioma hybrid cells, cerebellar granule cells, and selected human L1-transfected murine fibroblasts (Charness et al., 1994; Ramanathan et al., 1996; Wilkemeyer and Charness, 1998; Wilkemeyer et al., 1999). Similar concentrations of ethanol also inhibited L1-mediated neurite outgrowth in cerebellar granule cells (Bearer et al., 1999).

Structure activity analysis of various straight-chain, branched-chain, and cyclic alcohols revealed surprisingly strict structural requirements for alcohol inhibition of L1-mediated cell-cell adhesion (Wilkemeyer et al., 2000). The potency of methanol, ethanol, 1-propanol, and 1-butanol increased as a function of carbon chain length and membrane-buffer partition coefficient (Charness et al., 1994; Ramanathan et al., 1996). In contrast, 1-pentanol and higher 1-alcohols had no effect on L1-mediated cell-cell adhesion. The activity of 1-butanol, a four-carbon 1-alcohol, was abolished by the presence of a double bond between the 3 and 4 carbons; however, the presence of methyl groups at the 2 or 3 carbons was associated with an increase in potency (Wilkemeyer et al., 2000). These findings indicate that ethanol and other small alcohols inhibit L1-mediated cell-cell adhesion by binding within a well-defined, hydrophobic pocket of a target protein, possibly L1.

We believe that the existence of a specific binding pocket for ethanol would lead to the development of drugs that can block ethanol's effects. Strikingly, very low concentrations of both the five-carbon alcohol 1-pentanol and the eight-carbon alcohol 1-octanol abolished the effects of ethanol on L1-mediated cell-cell adhesion (Wilkemeyer et al., 2000). 1-Octanol also blocked the effects of ethanol on the morphology of dividing neural cells (Wilkemeyer et al., 2000) and prevented apoptosis and dysmorphology in cultured mouse embryos (Chen et al., 2001). 1-Octanol is a toxic compound that could not be used clinically. However, the identification of a single compound that blocks ethanol teratogenesis indicates the possibility of safer alcohol antagonists.

In U.S. Pat. No. 6,359,015 B1—Charness et al. (incorporated herein in its entirety by reference) a method and composition for antagonizing inhibition effects of alcohol on cell adhesion using 1-pentanol, 1-octanol, and derivatives thereof, was disclosed. The present invention identifies a new series of alcohol antagonists and examines their structure activity relation and mechanism of action.

U.S. Pat. Nos. 5,496,851; 6,169,071; and 6,169,072, are directed to method and compounds for modulating or inhibiting cell-cell-adhesion.

OBJECTS AND SUMMARY OF THE INVENTION

The principal object of the present invention is to provide a method and compound for antagonizing inhibition effects of alcohol on cell adhesion. This is based on the discovery that straight, branched, and cyclic alcohols act on multiple, discrete sites to antagonize the actions of ethanol and 1-butanol on L1-mediated cell-cell adhesion.

Another object of the present invention is to provide a method and compound for the prophylaxis or treatment of neurotoxic effects of alcohol, particularly beverage alcohol, i.e., ethanol.

An additional object of the present invention is to provide a method and compound for the prophylaxis or treatment of fetal alcohol syndrome, memory disorders, malformations of the brain, cognitive learning disorders, neuro-behavioral disorders, neurological disorders, teratogenesis, and alcohol-related memory disorder, and alcohol addiction in adults.

In accordance with the present invention, a method of antagonizing inhibition effects of alcohol on cell adhesion, includes contacting a cell-adhesion molecule expressing cell with an effective amount of a compound, wherein the compound comprises an alcohol with five or more carbons. More particularly, the compound comprises 3-pentanol, 2-pentanol, cyclopentanol, 4-methyl-1-pentanol, 2-methyl-2-pentanol, decanol, 2,6-diisopropylphenol, or a structural derivative thereof.

BRIEF DESCRIPTION OF THE DRAWINGS

The above and other objects, novel features and advantages of the present invention will become apparent from the following detailed description of the invention, as illustrated in the drawings, in which.

DETAILED DESCRIPTION OF THE INVENTION

The present invention is based on the discovery that 1-octanol antagonizes ethanol inhibition of L1-mediated cell adhesion and prevents ethanol teratogenesis in mouse whole embryo culture. The present invention identifies a new series of alcohol antagonists and demonstrates their mechanism of action.

Figure 1:
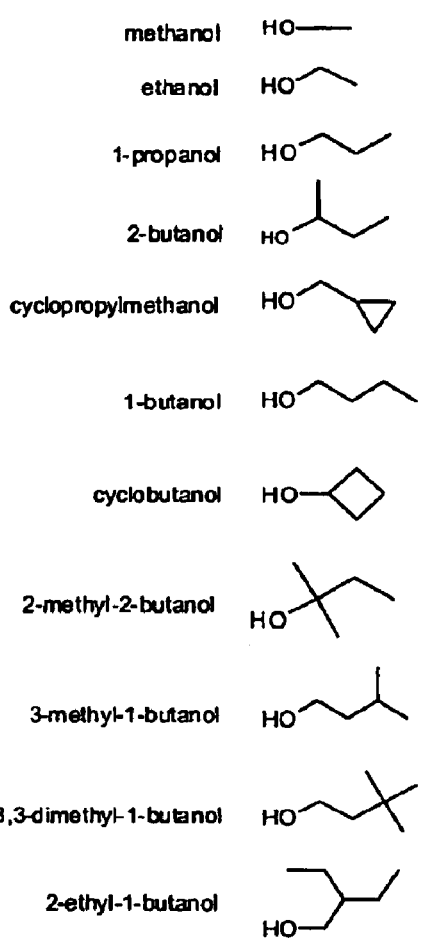
FIG. 1 illustrates structural activity relationship of various alcohols.
Figure 1:
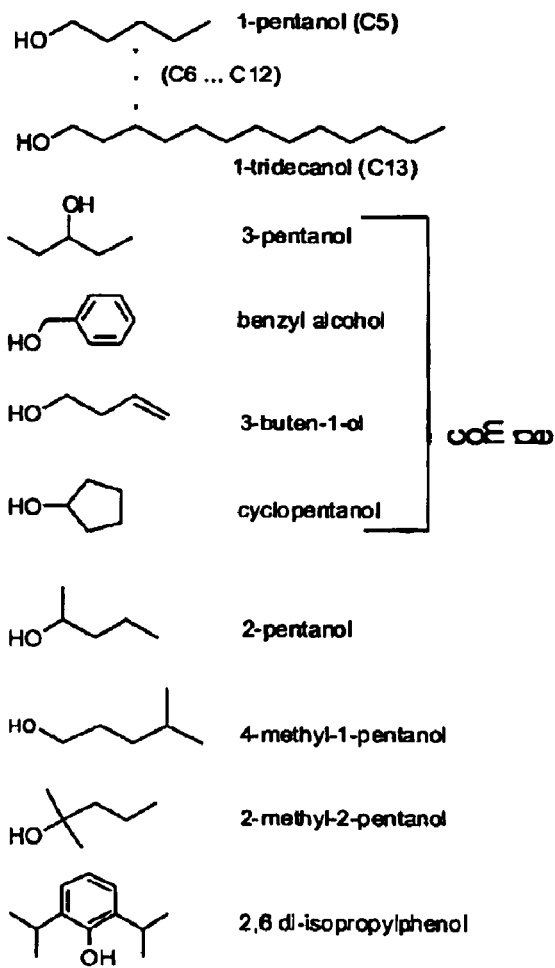
Figure 1:
Figure 1:
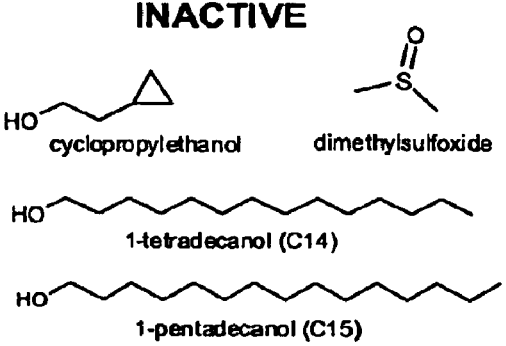

FIG. 1 shows the structure of the agonist and antagonist molecules discussed in this invention, wherein alcohols are categorized as Agonists (inhibit L1-mediated cell-cell adhesion), Antagonists (block the actions of agonists), Mixed Agonist-Antagonist (inhibit L1-mediated cell-cell adhesion at lower potency than predicted with weak antagonist activity at low concentrations) or inactive (having neither agonist nor antagonist activity).

Cell aggregation assays were carried out in ethanol-sensitive, human L1-transfected NIH/3T3 cells in the absence and presence of 100 mM ethanol or 2 mM 1-butanol and candidate antagonists. Antagonist potency for 1-alcohols increased progressively over five-log orders from 1-pentanol (C5) to 1-dodecanol (C12). Antagonist potency declined from 1-dodecanol (C12) to 1-tridecanol (C13), and 1-tetradecanol (C14) and 1-pentadecanol (C15) were inactive.

The presence and position of a double bond in the 1-butanol molecule determined whether a compound was a full agonist (1-butanol), a mixed agonist-antagonist (2-buten-1-ol), or an antagonist (3-buten-1-ol). Increasing the concentration of agonist (1-butanol or ethanol) overcame the antagonism of 3-buten-1-ol, benzyl alcohol, cyclopentanol and 3-pentanol, but not that of 4-methyl-1-pentanol, 2-methyl-2-pentanol, 1-pentanol, 2-pentanol, 1-octanol and 2,6-di-isopropylphenol (propofol), showing that the mechanisms of antagonism may differ between these groups of compounds. These findings indicate that selective straight, branched, and cyclic alcohols act at multiple, discrete sites to antagonize the actions of ethanol and 1-butanol on L1-mediated cell-cell adhesion.

EXAMPLE 1

This example illustrates inhibition of cell-cell adhesion by various alcohols.

Reagents

Alcohols were obtained from Sigma-Aldrich (Sigma Chemical Company, St. Louis, Mo.). All other chemicals were obtained from Sigma or as indicated. Most alcohols were diluted in phosphate buffered saline (PBS, 0.13M NaCl, 0.003M KCl, 0.01M $Na_2HPO_4$, 0.002M $KH_2PO_4$) or dimethyl sulfoxide (DMSO), as indicated.

Cell Culture

NIH/3T3 cells were cultured at 37° C. in Dulbecco's minimum Eagle medium (DMEM) (Invitrogen, Carlsbad, Calif.) supplemented with 10% normal calf serum (Intergen, Purchase, N.Y.) and 400 μg/ml G418 (Life Technologies), in an atmosphere of 90% air and 10% $CO_2$. Three subclones were utilized in these studies: 2B2-L1, 2A2-L1 and Vec-1A5. The 2B2-L1 and 2A2-L1 cell lines are ethanol sensitive subclones derived from a stable transfection of NIH/3T3 cells with human L1 cDNA; Vec-1A5 is a subclone from a transfection with the empty expression vector (Wilkemeyer and Charness, 1998).

Cell Adhesion Assay

Cell adhesion assays were performed in the absence and presence of the compounds, listed below in Table 1. Antagonist activity was measured against 100 mM ethanol for all of the compounds or against 2 mM 1-butanol, where indicated. The aqueous concentration of each antagonist was calculated to produce membrane concentrations equivalent to 100 mM ethanol. Membrane/buffer partition coefficients ($P_{m/b}$) were obtained or calculated from published octanol/water partition coefficients. The compounds are sorted by decreasing membrane/buffer partition coefficients. The $P_{m/b}$ for ethanol is 0.096 and for 1-butanol is 1.52.

Cell-cell adhesion was measured using a modified short-term aggregation assay of sub-confluent cells (Wilkemeyer and Charness, 1998; Wilkemeyer et al., 2000). Cells were detached by gentle agitation in calcium-free and magnesium-free PBS supplemented with 0.1 mg/ml. DNase, mechanically dissociated to obtain a single-cell suspension, and diluted to 350,000 cells/ml. One ml of the cell suspension was added per well (4.5 $cm^2$) to a 12-well plate. Agonists and test antagonists were added simultaneously, plates were sealed with parafilm to prevent evaporation, and the cells were gently shaken for 30 minutes at room temperature or on ice. Cells were viewed at a final magnification of 200× and each well was scored for single and adherent cells in five to six microscopic fields of view. Approximately 100 cells per field of view and 600 cells per well were counted. The percent of adherent cells was calculated for each microscopic field of view and then averaged for each well.

Agonists and antagonists were initially tested at aqueous concentrations that were calculated to produce molar membrane concentrations (~10 mM) equivalent to those produced by an aqueous concentration of 100 mM ethanol ($EC_{EQ}$). Calculations were based on membrane-buffer partition coefficients ($P_{m/b}$), which were obtained from a published source (McCreery and Hunt, 1978) or were derived by dividing the octanol/water partition coefficient by five.

L1-mediated cell-cell adhesion was defined as the difference in percent of adherent cells between an L1-transfected cell line (2B2-L1 or 2A2-L1) and a vector-transfected cell line (Vec-1A5). This component of cell adhesion is fully inhibited by Fab fragments of an anti-L1 polyclonal antibody (Wilkemeyer and Charness, 1998). Agonist inhibition of cell adhesion was calculated as 100×(1—the ratio of L1-mediated cell-cell adhesion in the presence and absence of agonist).

Agonists include compounds that inhibit L1-mediated cell-cell adhesion. Antagonists include compounds that have no effect on L1-mediated cell-cell adhesion and block the action of agonists. Molecules that are neither agonists nor antagonists are referred to as inactive. Antagonist activity was calculated as 100×(1-((% inhibition cell adhesion by agonist plus antagonist)/(% inhibition cell adhesion by agonist))).

EXAMPLE 2

The following is an example of structure activity analysis of alcohol antagonists.

The antagonists 1-pentanol and 1-octanol structurally resemble the agonist 1-butanol (FIG. 1), but do not inhibit L1-mediated cell-cell adhesion (Wilkemeyer et al., 2000). We hypothesized that other molecules that resemble agonists, but do not inhibit L1-mediated cell-cell adhesion, would also be antagonists. Each candidate antagonist was tested at a single aqueous concentration that was calculated to produce a molar membrane concentration equivalent to that produced by a buffer solution of 100 mM ethanol ($EC_{EQ}$). This concentration of ethanol maximally inhibited (62±7%) L1-mediated cell-cell adhesion. Most of the candidate molecules blocked more than 60% of the activity of 100 mM ethanol or 2 mM 1-butanol (see Table 1 below). In contrast, at the $EC_{EQ}$ (aqueous concentration that produces molar membrane concentration equivalent to 100 mM ethanol) (see Table 1 below) and at 10 times the $EC_{EQ}$, DMSO, cyclopropylethanol, 1-tetradecanol, and 1-pentadecanol were neither agonists nor antagonists. To confirm that alcohols did not have an effect on the non-L1 component of cell adhesion, we performed aggregation assays on NIH/3T3 cells transfected with an empty vector. The mean±S.E.M. percent cell adhesion for four independent assays was as follows: control, 15±1; 6 mM 1-butanol, 13±2; 50 $\mu$M 1-octanol, 12±1; 10 mM 3-buten-1-ol, 14±0; 0.7 mM 1-pentanol, 16±2; 0.7 mM 4-methyl-1-pentanol, 15±3; and 1% DMSO, 13±0.

Compounds Related to 1-Butanol

Figure 2:
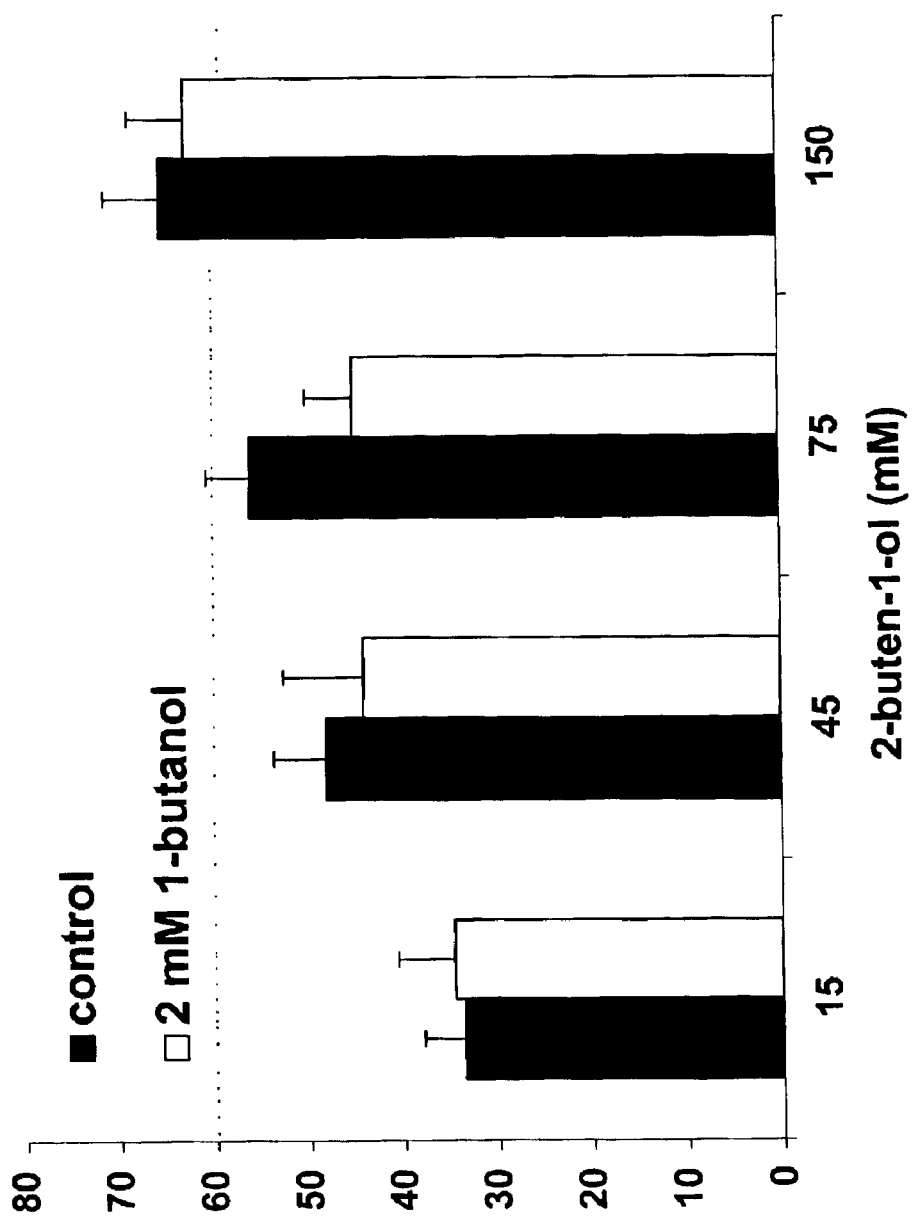
FIG. 2 illustrates agonist and antagonist effects of 2-buten-1-ol.

3-Buten-1-ol differs from 1-butanol only by the presence of a double bond between the number 3 and 4 carbon atoms. Alone, 3-buten-1-ol had no effect on L1-mediated cell-cell adhesion (Wilkemeyer et al., 2000); however, 9.6 mM 3-buten-1-ol ($EC_{EQ}$) blocked 64±16% of the agonist activity of 100 mM ethanol (see Table 1 below). The presence of a double bond between the 2 and 3 carbons in 1-butanol had a different effect. As shown in FIG. 2, cell adhesion assays were performed in human L1-expressing NIH/3T3 cells in the presence of the indicated aqueous concentrations of 2-buten-1-ol and in the absence (control, solid bar) or presence (open bar) of 2 mM 1-butanol. Bars represent the mean±SEM for the percent inhibition of cell adhesion from 4 to 11 independent experiments. The horizontal dashed line indicates the mean percent inhibition of cell adhesion by 2 mM 1-butanol alone (60±5%, n=11). The inhibition of cell adhesion produced by 15 mM 2-buten-1-ol plus 1-butanol (35+6%, n=11) and by 15 mM 2-buten-1-ol alone (34±4%, n=10) was significantly less than that produced by 2 mM 1-butanol alone (paired t-test, t=5.21, 5.31, respectively; p<0.001).

At a concentration of 15 mM ($EC_{EQ}$), 2-buten-1-ol partially inhibited L1-mediated cell-cell adhesion, but also partially antagonized the actions of 1-butanol and ethanol (FIG. 2). At higher concentrations (150 mM), 2-buten-1-ol maximally inhibited L1-mediated cell-cell adhesion and neither antagonized nor augmented the actions of 1-butanol or ethanol. Of note, 11 mM ($EC_{EQ}$) 2-butanol, which resembles 1-butanol and 1-propanol, was a full agonist (63±9% inhibition, n=6) and had no antagonist activity.

Cutoff Effect for Antagonist 1-Alcohols

1-Octanol is a two hundred-fold more potent antagonist than 1-pentanol (FIG. 3)(Wilkemeyer et al., 2000). 1-Octanol is also thirty-seven-fold more lipid soluble than 1-pentanol (see Table 1 below). These data show that 1-octanol and 1-pentanol interact with a hydrophobic moiety within a putative antagonist binding site. We therefore determined whether the antagonist potency for 1-alcohols increases as a function of chain length and membrane-buffer partition coefficient and if there is a cutoff above which longer 1-alcohols are less potent or inactive.

An artificial cutoff can be observed if a series of increasingly hydrophobic alcohols are incompletely soluble in water. To avoid this, we evaluated DMSO as a solvent for the 1-alcohols. 120 mM (1%) DMSO did not inhibit L1-mediated cell adhesion, nor did it antagonize ethanol inhibition of L1-mediated cell-cell adhesion (see Table 1 below). At the concentrations employed in our experiments, all 1-alcohols were soluble in DMSO.

Figure 3:
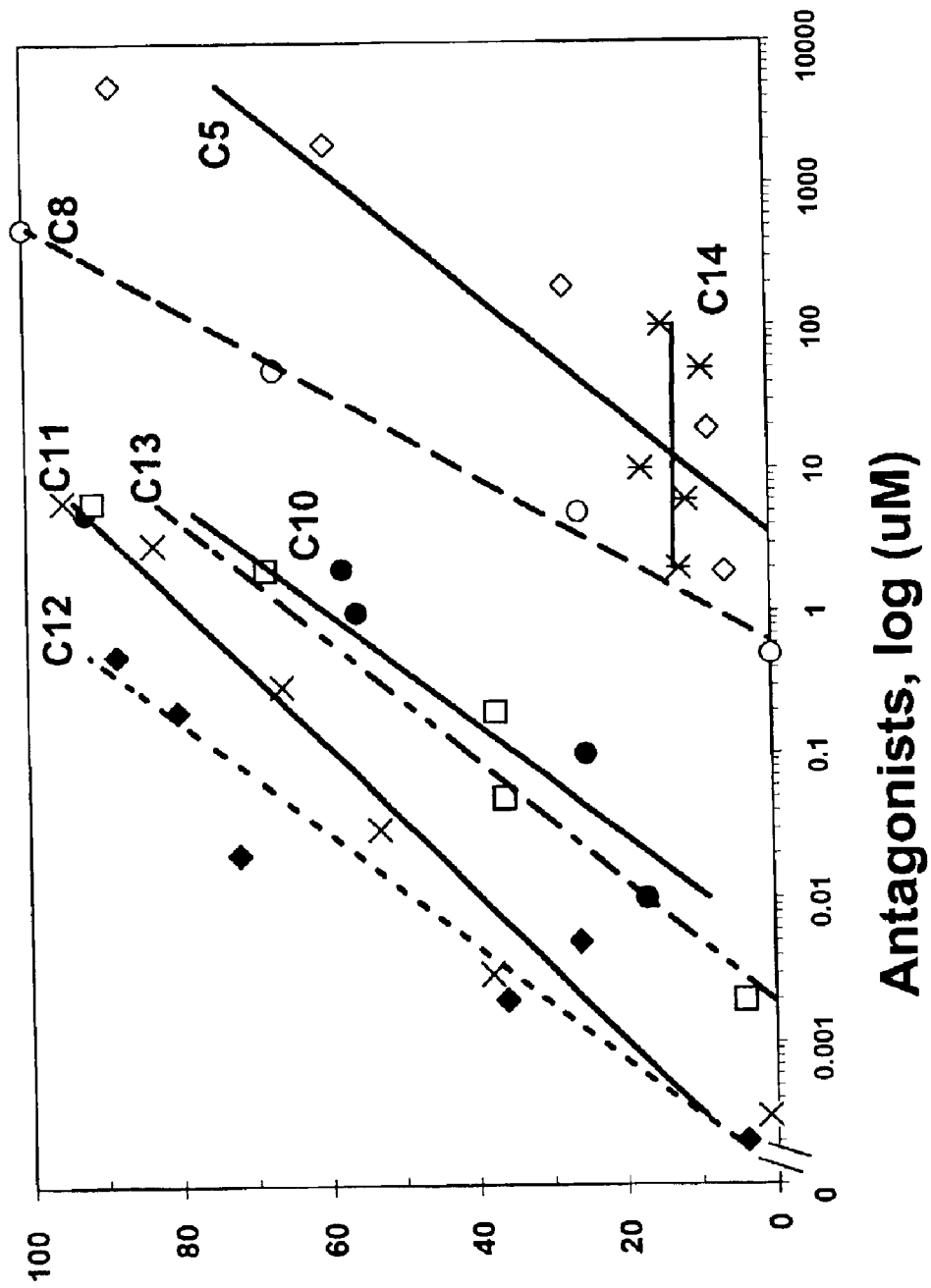
FIG. 3 illustrates antagonist effects of long-chain alcohols.

Concentration-response curves were determined for antagonism of ethanol (100 mM) inhibition of L1-mediated cell-cell adhesion by a series of 1-alcohols dissolved in 1% DMSO (FIG. 3). Cell adhesion assays were performed in human L1-expressing NIH/3T3 cells in the presence of ethanol (100 mM) and the indicated aqueous concentrations of long-chain alcohols (antagonists). FIG. 3 shows the means for the antagonist activity of the indicated alcohols (n=4–16). Lines are fit by log-linear regression analysis. Shown in parentheses are $EC_{50}$s ($\mu$M) based on the aqueous concentrations and $EC_{50}$s ($\mu$M) based on calculated membrane concentrations and expressed relative to 1-pentanol, as determined from the $P_{m/b}$ ($EC_{50}$ aqueous, $EC_{50}$ membrane). In FIG. 3, open diamond (C5) indicates 1-pentanol (540, 540); open circle (C8) indicates 1-octanol (3, 98); filled circle (C10) indicates 1-dodecanol (0.4, 140); cross (C11) indicates 1-undecanol (0.03, 20); filled diamond (C12) indicates 1-dodecanol (0.01, 28); open square (C13) indicates 1-tridecanol (0.25, 1625); and asterisk (C14) indicates 1-tetradecanol. 1-Pentadecanol (C15) exhibited no antagonist activity (see Table 1 below).

As can be observed from FIG. 3, antagonist potency increased progressively over five-log orders from 1-pentanol (C5) to 1-undecanol (C11). The potency of 1-dodecanol (C12) was only slightly greater than that of C11, whereas 1-tridecanol (C13) was approximately 25 fold less potent than C12. 1-Tetradecanol (C14) showed only minimal antagonist activity and 1-pentadecanol (C15) was completely inactive (see Table 1 below). Because the test concentrations of C14 and C15 were very low (80 nM and 2.7 nM respectively), we also tested higher concentrations (2 $\mu$M to 10 $\mu$M) to ensure that we did not miss an antagonist effect. Even at these higher concentrations, C14 and C15 were inactive.

4-Methyl-1-Pentanol, a Bivalent Antagonist

Figure 4:
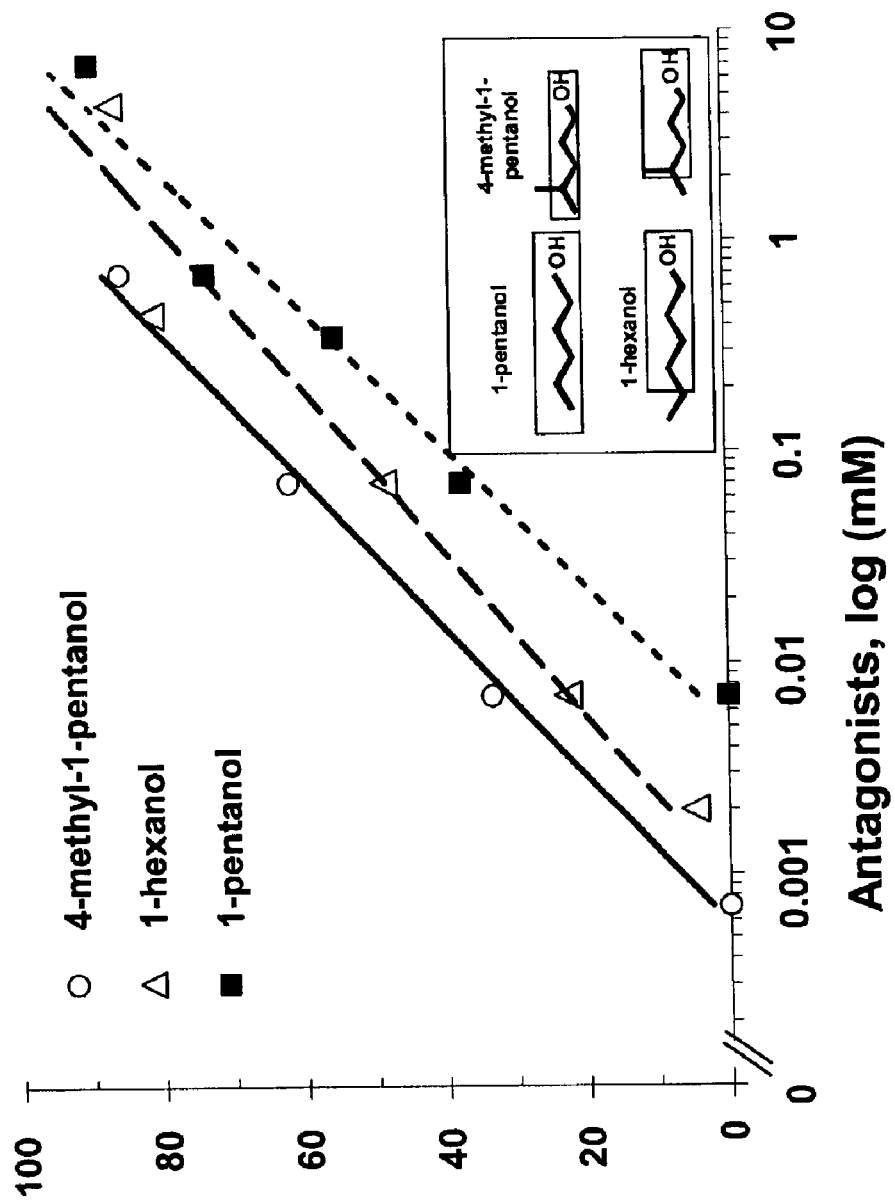
FIG. 4 illustrates antagonism of 1-butanol effects by 1-pentanol, 1-hexanol, and 4-methyl-1-pentanol.

Molecules that contain multiple representations of 1-butanol were more potent agonists than 1-butanol (Wilkemeyer et al., 2000), consistent with the hypothesis that agonists interact with a selective recognition site. If the antagonist site is similarly selective, then molecules that contain multiple representations of an antagonist should be more potent than the antagonist itself. 4-Methyl-1-pentanol can present a 1-pentanol molecule to a putative antagonist site from two different orientations (FIG. 4-inset).

Cell adhesion assays were performed in human L1-expressing NIH/3T3 cells in the presence of 1-butanol (2 mM) and the indicated (FIG. 4) concentrations of 1-pentanol, 4-methyl-1-pentanol or 1-hexanol. FIG. 4 shows the mean±SEM antagonist activity for the indicated aqueous concentrations of 4-methyl-1-pentanol (circle), 1-hexanol (triangle), and 1-pentanol (square). FIG. 4-inset shows the location of 1-pentanol molecules within the parent structures outlined by box. It is noted that 4-methyl-1-pentanol, which can present a 1-pentanol moiety from two possible orientations, is approximately four-fold more potent than 1-pentanol, after adjusting for differences in calculated membrane concentration (see Results: 4-methyl-1-pentanol, a bivalent antagonist).

Concentration-response curves were determined for 1-pentanol and 4-methyl-1-pentanol antagonism of 2 mM butanol inhibition of L1-mediated cell-cell adhesion. 1-Hexanol was used as a control for the number of carbons in 4-methyl-1-pentanol. Antagonist potency was estimated from a linear regression analysis of the antagonist concentration-response curves. The aqueous concentration of 4-methyl-1-pentanol that produced half maximal effect (32 $\mu$M) was approximately 7-fold greater than that of 1-pentanol (223 $\mu$M), and approximately 2.5 times that of 1-hexanol (80 $\mu$M) (FIG. 4). These ratios were then adjusted, based on the membrane buffer partition coefficient, to take into account the difference in membrane concentration of each antagonist. With this correction, 4-methyl-1-pentanol was approximately 3.7-fold more potent than 1-pentanol, whereas 1-hexanol was only 0.7-fold as potent as 1-pentanol.

EXAMPLE 3

The following illustrates multiple mechanisms of antagonism.

We showed previously that when tested in NIH/3T3 cells against a sub-maximally effective concentration of 1-octanol, increasing concentrations of 1-butanol reduced, but did not eliminate, the antagonist effect of 1-octanol (Wilkemeyer et al., 2000). This finding indicated that 1-octanol was a non-competitive antagonist. We used L1-expressing NIH/3T3 cells in the presence of increasing concentrations of 1-butanol to investigate the mechanism of inhibition for various antagonists (FIG. 5B) and two structurally dissimilar antagonists, 3-buten-1-ol and 1-octanol (FIG. 5A).

Figure 5A:
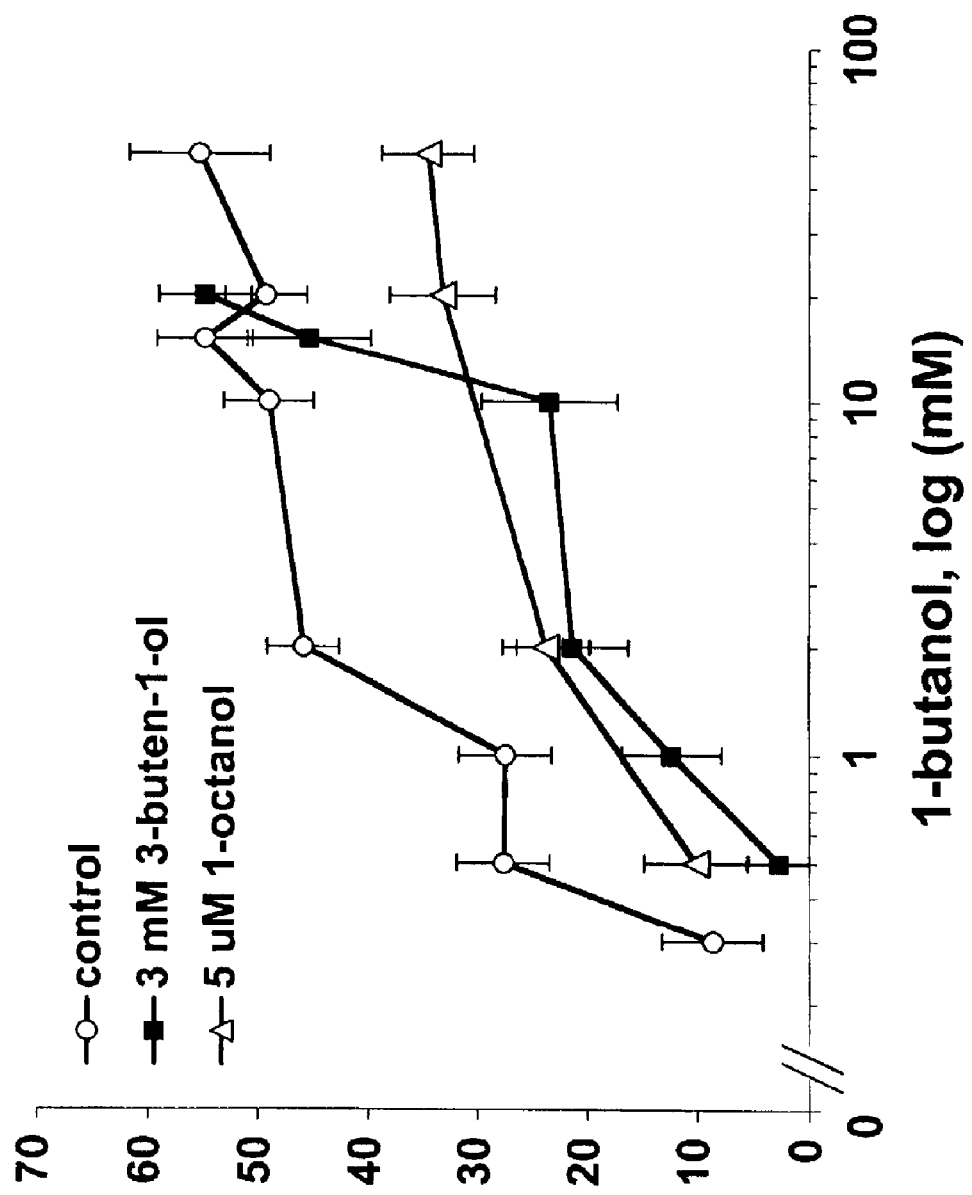
FIG. 5A shows concentration-response curves for 1-butanol inhibition of cell-cell adhesion.

FIG. 5A shows concentration-response curves for 1-butanol inhibition of cell-cell adhesion (control, O) determined in the presence of $IC_{50}$ concentrations for 3-buten-1-ol (3 mM)(■) and 1-octanol (5 $\mu$M) (⇌). Shown is the mean±SEM percent inhibition of cell adhesion for five to twelve experiments. It is noted that increasing concentrations of 1-butanol eliminate antagonism by 3-buten-1-ol, but not by 1-octanol.

Concentration-response curves for 1-butanol inhibition of L1-mediated cell-cell adhesion revealed that 2 mM 1-butanol produced approximately 90% of the maximal agonist response (FIG. 5A). Concentrations of 1-butanol above 75 mM altered membrane morphology and therefore were not used. Increasing concentrations of 1-butanol progressively reduced and then eliminated the antagonist effect of 3 mM 3-buten-1-ol. In contrast, increasing concentrations of 1-butanol did not eliminate the antagonist effect of 5 $\mu$M 1-octanol. These experiments indicate that alcohol inhibition of L1-mediated cell-cell adhesion can be antagonized through different mechanisms.

Figure 5B:
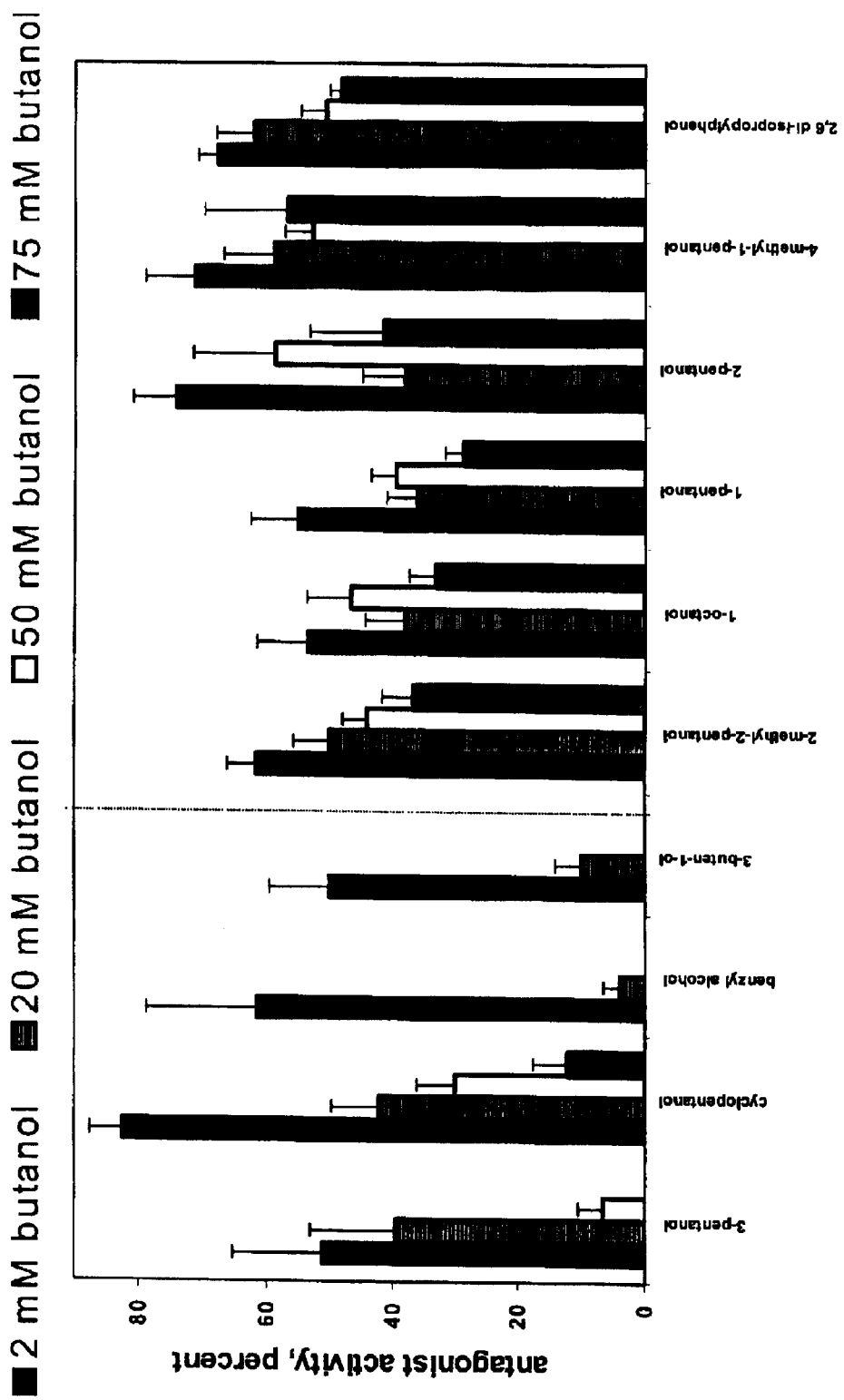
FIG. 5B shows the mean±SEM percent antagonist activity for the indicated compounds against 2 mM (first bar—solid), 20 mM (second bar—horizontal lines), 50 mM (third bar—white), and 75 mM (fourth bar—gray) 1-butanol (n=3–14)

We next studied the mechanisms of inhibition for ten different antagonists. Each antagonist was tested at a concentration that blocked 50% to 80% of the actions of 2 mM 1-butanol (FIG. 5B). Concentration-response curves for 1-butanol (0–75 mM) were determined in the absence and presence of a single concentration of each antagonist (FIG. 5B). FIG. 5B shows the mean±SEM percent antagonist activity for the indicated compounds against 2 mM (solid), 20 mM (horizontal lines), 50 mM (white), and 75 mM (gray) 1-butanol (n=3–14). The dashed vertical line separates antagonists whose actions were overcome by increasing concentrations of 1-butanol (left) from those that were not (right). Most of the antagonists were tested at aqueous concentrations that produce the same molar membrane concentration as an aqueous solution of 50–100 mM ethanol. For 3-buten-1-ol (3000 $\mu$M), 1-octanol (5 $\mu$M), 1-pentanol (700 $\mu$M) and 4-methyl-1-pentanol (40 $\mu$M) the approximate $EC_{50}$ (against 2 mM 1-butanol) was used. The remaining concentrations were as follows: 3-pentanol (2000 $\mu$M), cyclopentanol (4300 $\mu$M), benzyl alcohol (3800 $\mu$M), 2-methyl-2-pentanol (1800 $\mu$M), 2-pentanol (2200 $\mu$M), 2,6 di-isopropylphenol (2 $\mu$M).

As shown in FIG. 5B, increasing concentrations of 1-butanol eliminated the antagonist activity of 3-pentanol, cyclopentanol, benzyl alcohol, and 3-buten-1-ol. In contrast, concentrations of up to 75 mM butanol did not eliminate the antagonist activity of 2-methyl-2-pentanol, 1-octanol, 1-pentanol, 2-pentanol, 4-methyl-1-pentanol and 2,6-di-isopropylphenol (propofol). The two groups of compounds did not differ in their antagonism of 2 mM 1-butanol.

Our search for antagonists was guided by observations on the properties of agonists (Wilkemeyer et al., 2000). The above examples show that the potency of 1-alcohols increased as a function of chain length with an abrupt cutoff between 1-butanol and 1-pentanol. 1-Butanol was both the most potent 1-alcohol and also the most constrained, its activity being readily altered by minor chemical modifications. Restriction of movement between the 3 and 4 carbons of 1-butanol (e.g., 3-buten-1-ol or cyclopropylethanol) or the placement of methyl groups adjacent to the hydroxyl group of 1-butanol (e.g. 2-pentanol and 2-methyl-2-pentanol) abolished agonist activity. In contrast, the presence of methyl or ethyl groups at the 2 or 3 carbons increased agonist potency (e.g. 3-methyl-1-butanol, 2-ethyl-1-butanol, or 3,3-dimethyl-1-butanol). These data indicate that interactions near the number 1 and 4 carbons of 1-butanol are critical for agonist activity.

The marked sensitivity of 1-butanol activity to chemical modification was most apparent in experiments with 2-buten-1-ol and 3-buten-1-ol. The presence of a double bond between the 2 and 3 carbons of 1-butanol converted a full agonist (1-butanol) to a mixed agonist-antagonist (2-buten-1-ol). 2-Buten-1-ol inhibited L1-mediated cell-cell adhesion, albeit with lower potency than expected based on predicted membrane concentration. At low concentrations, 2-buten-1-ol partially inhibited L1-mediated cell-cell adhesion and partially antagonized the agonist activity of 1-butanol. At higher concentrations, 2-buten-1-ol acted as a full agonist and did not antagonize the actions of 1-butanol. Moving the double bond of 2-buten-1-ol from the number 2–3 carbons to the number 3–4 carbons transformed the molecule from a mixed agonist-antagonist to a competitive antagonist, 3-buten-1-ol. Therefore, the presence and position of a double bond determined whether the resulting molecule is a potent agonist (1-butanol), a mixed agonist-antagonist (2-buten-1-ol), or a competitive antagonist (3-buten-1-ol).

1-Propanol appears to be a less constrained agonist than 1-butanol. The presence of a methyl group adjacent to the hydroxyl group of 1-propanol (2-butanol) or the restriction of movement between the 2 and 3 carbons (cyclopropylmethanol) did not affect agonist activity. However, placement of an ethyl group adjacent to the hydroxyl group of 1-propanol converted this molecule from an agonist to an antagonist (3-pentanol). Thus, even for the smaller 1-propanol molecule, sufficiently large substitutions in the vicinity of the hydroxyl group may produce steric hindrance and retard agonist interactions.

Figure 6B:
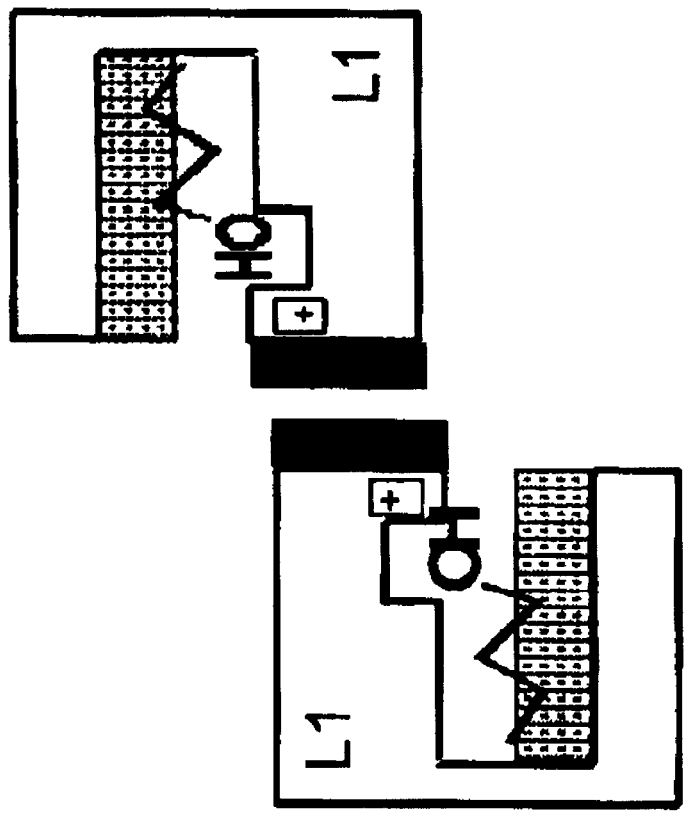
FIG. 6B shows a model that agonists, illustrated with 1-butanol, must bind to a hydrophobic recognition site.
Figure 6A:
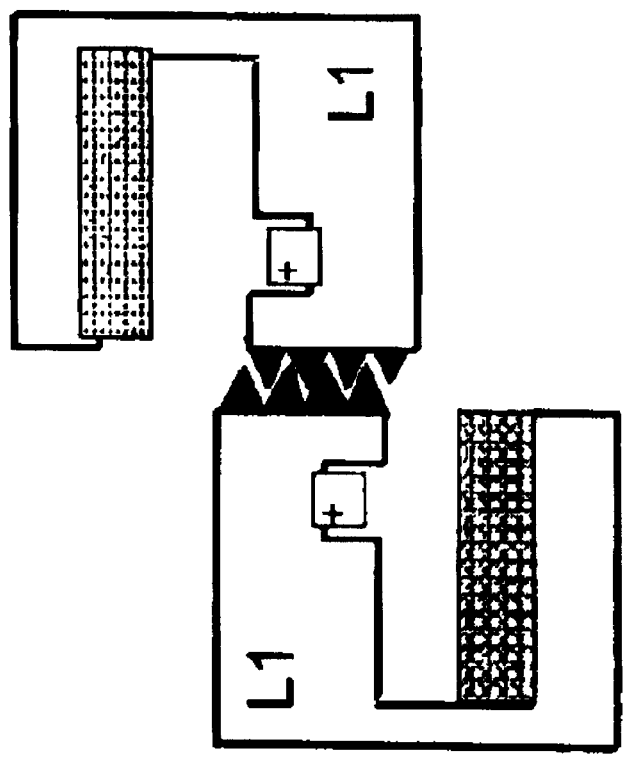
FIG. 6A shows a model of homophilic binding of L1 molecule.
Figure 6D:
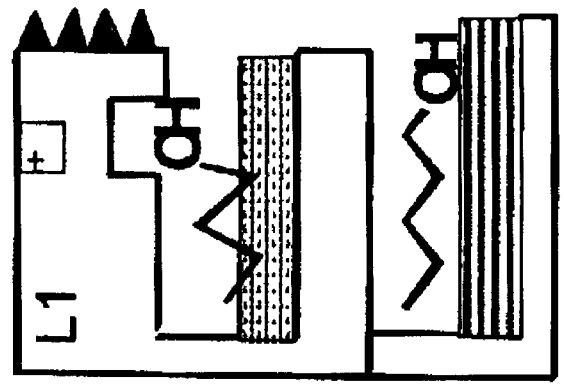
FIG. 6D shows a model that non-competitive antagonists, illustrated with 1-pentanol, may bind to a second hydrophobic site.
Figure 6C:
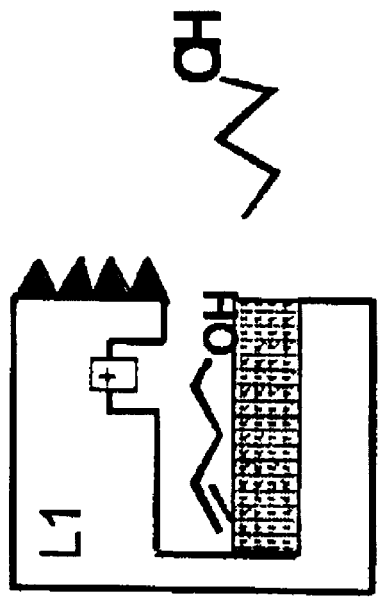
FIG. 6C shows a model that competitive antagonists, illustrated with 3-buten-1-Ol, competes for agonist binding at the hydrophobic agonist recognition site.

Our data illustrate a model for agonist and antagonist effects on L1-mediated cell-cell adhesion (Wilkemeyer et al., 2000)(FIGS. 6A-D). FIG. 6A shows homophilic binding of L1 molecules. A putative homophilic binding site is depicted with a teeth-like structure. FIG. 6B shows that agonists, illustrated with 1-butanol, must bind to a hydrophobic recognition site (hash-marked box) and orient their hydroxyl groups towards a hydrophilic allosteric site (plus sign), producing a conformational change, perhaps in L1, that leads to reduced L1-mediated cell-cell adhesion. FIG. 6C shows that competitive antagonists, illustrated with 3-buten-1-ol, compete for agonist binding at the hydrophobic agonist recognition site, but are unable to orient their hydroxyl groups towards the allosteric site. Finally, FIG. 6D shows that non-competitive antagonists, illustrated with 1-pentanol, may bind to a second hydrophobic site (lined box), at which they produce a conformational change that alters the relation of the agonist recognition site to the allosteric site. These models depict L1 as the target protein, but the agonist and antagonist sites may reside on other proteins that interact with L1.

We show the existence of an agonist target comprising a discrete hydrophobic binding site adjacent to a hydrophilic allosteric site. Agonist effects occur only when a molecule binds to the hydrophobic site and orients its hydroxyl group towards the allosteric site. The agonist target can be envisioned as a 1-butanol receptor that narrowly accommodates a flexed 1-butanol molecule. Restricting movement between the 3 and 4 carbons of 1-butanol may abolish agonist activity by preventing bound 1-butanol from presenting its hydroxyl group to the allosteric site. An extended conformation of 1-butanol (3-buten-1-ol) or longer 1-alcohols (e.g. 1-pentanol) may be inactive as agonists because they are unable to bind coordinately to closely spaced hydrophobic and hydrophilic allosteric sites. Methanol, ethanol, and 1-propanol may be less potent than 1-butanol, because they are less hydrophobic and bind with lower affinity to the hydrophobic site. However, because they are small enough to maintain the correct orientation between their hydrophobic methylene groups and hydrophilic hydroxyl groups, they are still agonists.

A requirement for coordinate binding to two sites may also support the observation that substituents adjacent to the hydroxyl group reduce agonist activity. Because the 1-butanol molecule is already a "tight fit", even minor degrees of steric hindrance might disrupt hydrogen acceptor activity at the allosteric site; in contrast, the less constrained 1-propanol molecule tolerates a methyl group, but not an ethyl group adjacent to the hydroxyl group. The existence of a 1-butanol receptor would also explain why molecules that present a butanol moiety from multiple orientations are more potent agonists than 1-butanol (Wilkemeyer et al., 2000). For these divalent (3-methyl-1-butanol, 2-ethyl-1-butanol) and trivalent (3,3-dimethyl-1-butanol) 1-butanol molecules, the probability of presenting a 1-butanol moiety in the correct orientation to a 1-butanol receptor is greater than for 1-butanol.

A somewhat different picture of an antagonist binding site emerges from the structure activity analysis of various antagonist alcohols. Most of the alcohols tested for antagonist activity were selected because they resembled agonists, but did not inhibit L1-mediated cell-cell adhesion. The majority of these alcohols proved to be antagonists, although there were a few exceptions. 2-buten-1-ol, which resembles 1-butanol, was a mixed agonist-antagonist. Cyclopropylethanol, which resembles the agonist cyclopropylmethanol, was inactive (neither an agonist nor an antagonist). One compound, propofol, does not clearly resemble any of the agonists, but was also an antagonist.

The membrane-buffer partition coefficients of the 1-alcohols increase with carbon chain length, and the series of 1-alcohols showed a striking increase in antagonist potency between C5 and C12. These data indicate that the antagonist 1-alcohols interact with a hydrophobic target site. Antagonist potency decreased between C12 and C13, and C14 and C15 showed little or no antagonism. The 1-alcohols from C13 to C15 are significantly more hydrophobic than the 1-alcohols from C5 to C12; therefore, the loss of activity with increasing carbon chain length indicates that the antagonist effect of C5 to C12 is not solely the result of their interaction with membrane lipids. More likely, these 1-alcohol antagonists target a cellular protein and bind within a hydrophobic pocket of restricted size. In contrast to the agonist site, which shows an abrupt cutoff between 1-butanol and 1-pentanol, the antagonist site shows a more gradual loss of recognition or binding of higher 1-alcohols. Because all of these alcohols were soluble in DMSO at the concentrations employed, it is unlikely that this cutoff is an artifact of the increasing insolubility of the longer 1-alcohols.

If antagonists bind to a structurally-selective site, then ligands that present an antagonist configuration from more than one orientation have a higher probability of correctly engaging the binding pocket. This may explain why the antagonist potency of 4-methyl-1-pentanol, which can present a 1-pentanol molecule from two different orientations, was greater than that of 1-pentanol. The two compounds differ only slightly in membrane-buffer partition coefficient (see Table 1 below). Therefore, differential access to a hydrophobic site would not likely account for the difference in potency. Even after adjusting for the difference in membrane concentration predicted by partition coefficient, 4-methyl-1-pentanol was almost 4-fold more potent than 1-pentanol. A comparable discrepancy in agonist potency was observed between trivalent (3-3-dimethyl-1-butanol) and monovalent 1-butanol (Wilkemeyer et al., 2000).

The antagonist activity of four alcohols, 3-buten-1-ol, cyclopentanol, 3-pentanol, and benzyl alcohol, could be overcome by increasing concentrations of agonist. Each bears a close structural resemblance to a different alcohol agonist (FIG. 1). There are obvious similarities between 3-buten-1-ol and 1-butanol and between cyclopentanol and cyclobutanol. 3-Pentanol resembles the agonist 1-propanol, except for the presence of an ethyl group adjacent to the hydroxyl group. Benzyl alcohol, when aligned with 1-butanol, has features in common with 3-buten-1-ol, except that the ring structure assures that the double bond is shared between the 2–3 carbons and the 3–4 carbons. The structural similarity of these antagonists with alcohol agonists might enable them to compete for agonist binding at a common hydrophobic binding site (FIG. 6C).

The antagonist activity of a second group of alcohols could not be surmounted by increasing concentrations of agonist. All six molecules, 1-pentanol, 4-methyl-1-pentanol, 1-octanol, 2,6,-di-isopropylphenol, 2-pentanol, and 2-methyl-2-pentanol, present a linear array of at least five carbons and may be too large to fit within a delimited agonist binding pocket. These antagonists may interact with a second target site to alter the spatial relation between the hydrophobic agonist binding site and the allosteric site (FIG. 6D). In this situation, the interaction of the agonist with the allosteric site would be impaired at all agonist concentrations. Non-competitive antagonism can also result from covalent or high-affinity binding of an antagonist to a receptor; however, this mechanism is not consistent with the rapid reversibility of 1-octanol's antagonist activity (Wilkemeyer et al., 2000). The inactivity of 1-tetradecanol, 1-pentadecanol, and cyclopropylethanol suggests that the antagonist binding sites discriminate both molecular size and molecular shape.

Our models depict alcohol modulation of cell-cell adhesion through direct interactions of agonists and antagonists with the L1 molecule (FIG. 6). Although this is one putative mechanism for alcohol effects on cell adhesion, it is not the only one. L1 also engages in heterophilic binding with a number of extracellular, transmembrane, and intracellular proteins (Crossin and Krushel, 2000), each of which might present alcohol binding sites. L1 is also phosphorylated at multiple sites, with important effects on L1 internalization and cell adhesion (Zisch et al., 1997; Kamiguchi and Lemmon, 1998). Conceivably, alcohols target the kinases or phosphatases that regulate the state of L1 phosphorylation or the sites at which proteins interact with L1 to alter its function. There is ample precedent for the regulation of ethanol sensitivity by phosphorylation. Phosphorylation modulates the response to ethanol for the glycine receptor (Mascia et al., 1998), NMDA receptor (Miyakawa et al., 1997; Anders et al., 1999), $GABA_A$ receptor (Hodge et al., 1999), mGluR5 metabotropic glutamate receptors (Minami et al., 1998), N-type and P/Q-type calcium channels (Solem et al., 1997), nerve growth factor (Hundle et al., 1997), nucleoside transporters (Coe et al., 1996), and serotonin 5-HT1c receptors (Sanna et al., 1994). Further research is recommended to learn the precise molecular targets of alcohol agonists and antagonists that modulate L1-mediated cell-cell adhesion.

The specificity of alcohol interactions with targets that regulate cell adhesion is unique among all defined neuronal targets of ethanol. Alcohols interact with discrete regions of the $GABA_A$ (Mihic et al., 1997) and □l$GABA_C$ receptors (Wick et al., 1998), strychnine-sensitive glycine receptor (Mascia et al., 1996; Mihic et al., 1997; Wick et al., 1998; Ye et al., 1998; Mascia et al., 2000), neuronal (McKenzie et al., 1995) and peripheral (Zhou et al., 2000) nicotinic acetylcholine receptors, G protein-linked inwardly rectifying potassium channels (Lewohl et al., 1999), Shaw2 potassium channel (Harris et al., 2000), and serotonin 5-HT3 receptors (Lovinger, 1999). Each of these targets exhibits different cutoffs for 1-alcohols. Mutagenesis studies of the glycine receptor indicate that the size of the alcohol cutoff is a function of the molecular volume of single amino acids at a key location within the ethanol binding site (Wick et al., 1998). Strikingly, ethanol itself is an antagonist for anesthetic actions at a mutated glycine receptor that is insensitive to ethanol, but retains sensitivity to other anesthetics, consistent with competition of ethanol and anesthetics for a single binding site (Beckstead et al., 2001). At least for the GIRK potassium channels, 1-octanol is not an ethanol antagonist (Lewohl et al., 1999). Taken together, these data indicate that a variety of neuronal proteins present alcohol binding pockets, but each one differs in its specificity for straight chain, branched chain, and cyclic alcohols.

TABLE 1

Antagonist activity, and membrane/buffer partition coefficient for a series of alcohols and a non-volatile anesthetic.

| Concentration ($\mu$M) | Alcohols | Antagonist Activity Ethanol % ± SEM | Butanol % ± SEM | P(m/b) |
|---|---|---|---|---|
| 2* | 1-pentadecanol | 6 ± 7 | — | 347560 |
| 2* | 1-tetradecanol | 12 ± 6 | — | 112468 |
| 0.26 | 1-tridecanol | 37 ± 10 | — | 36394 |
| 0.35 | 1-dodecanol | 82 ± 11 | — | 26979 |
| 3 | 1-undecanol | 89 ± 15 | — | 3810 |
| 5 | 1-decanol | 93 ± 4 | — | 1910 |
| 2* | 2,6-di-isopropyl phenol | 87 ± 7 | 68 ± 3 | 1233 |
| 16 | 1-nonanol | 95 ± 4 | — | 604 |
| 50 | 1-octanol | 67 ± 9 | 82 ± 13 | 189 |
| 190 | 1-heptanol | 104 ± 4 | — | 51.4 |
| 450 | 1-hexanol | 88 ± 5 | — | 21.4 |
| 1100 | 4-methyl-1-pentanol | 91 ± 8 | 95 ± 20 | 9.36 |
| 1800 | 2-methyl-2-pentanol | 82 ± 5 | 61 ± 4 | 5.2 |
| 700* | 1-pentanol | 58 ± 12 | 55 ± 7 | 5.02 |
| 2100 | 3-pentanol | 92 ± 6 | 59 ± 13 | 4.69 |
| 2200 | 2-pentanol | 75 ± 8 | 74 ± 7 | 4.38 |
| 3800 | benzyl alcohol | 87 ± 8 | 62 ± 17 | 2.52 |
| 4300 | cyclopentanol | 99 ± 1 | 83 ± 5 | 2.24 |
| 9600 | 3-buten-1-ol | 67 ± 12 | — | 1 |
| 11,600 | cyclopropylethanol | 19 ± 8 | — | 0.83 |
| 120,000* | dimethyl sulfoxide | 15 ± 16 | — | 0.012 |

*Aqueous concentration higher than that required to produce the same membrane concentration as 100 mM ethanol.

A pharmaceutical composition including 3-pentanol, 2-pentanol, cyclopentanol, 4-methyl-1-pentanol, 2-methyl-2-pentanol, decanol, 2,6-diisopropylphenol, or a structurally-related derivative thereof, may be prepared, in a conventional manner. In particular, a pharmaceutical composition made in accordance with the present invention would include 3-pentanol, 2-pentanol, cyclopentanol, 4-methyl-1-pentanol, 2-methyl-2-pentanol, 2,6-diisopropylphenol, or a structural derivative thereof in an amount sufficient to provide therapeutic and/or prophylactic benefit, in combination with one or more pharmaceutically or physiologically acceptable carriers, diluents or excipients. Compositions of the present invention may be formulated for any appropriate manner for administration, including, for example, oral, nasal, intravenous or intramuscular administration. Appropriate dosages, duration and frequency of administration would be determined by known factors, such as the condition of the patient, the type and severity of the disease and the method of administration.

While this invention has been described as having preferred ranges, steps, materials, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

REFERENCES

The following references, to the extent that they provide exemplary procedural or other details supplementary to those set forth herein, are specifically incorporated herein by reference.

Anders D L, Blevins T, Sutton G, Swope S, Chandler L J and Woodward J J (1999) Fyn tyrosine kinase reduces the ethanol inhibition of recombinant NR1/NR2A but not NR1/NR2B NMDA receptors expressed in HEK 293 cells. *J. Neurochem.* 72:1389–1393.

Bearer C F, Swick A R, O'Riordan M A and Cheng G (1999) Ethanol inhibits L1-mediated neurite outgrowth in postnatal rat cerebellar granule cells. *J. Biol. Chem.* 274:13264–13270.

Beckstead M J, Phelan R and Mihic S J (2001) Antagonism of inhalant and volatile anesthetic enhancement of glycine receptor function. *J. Biol. Chem.* 276:24959–24964.

Charness M E, Querimit L A and Diamond I (1986) *J. Biol. Chem.* 261:3164–3169.

Charness M E, Safran R M and Perides G (1994) Ethanol inhibits neural cell-cell adhesion. *J. Biol. Chem.* 269:9304–9309.

Charness M E, Simon R P and Greenberg D A (1989) Ethanol and the nervous system. *N. Engl. J. Med.* 321:442–454.

Chen S-Y, Wilkemeyer M F, Sulik K K and Charness M E (2001) Octanol antagonism of ethanol teratogenesis. *Faseb J.* 15(9): 1649–1651.

Coe I R, Dohrman D P, Constantinescu A, Diamond I and Gordon A S (1996) Activation of cyclic AMP-dependent protein kinase reverses tolerance of a nucleoside transporter to ethanol. *J. Pharmacol. Exp. Ther.* 276:365–369.

Crossin K L and Krushel L A (2000) Cellular signaling by neural cell adhesion molecules of the immunoglobulin superfamily. *Developmental Dynamics* 218:260–279.

Demyanenko G P, Tsai A Y and Maness P F (1999) Abnormalities in neuronal process extension, hippocampal development, and the ventriclar system of L1 knockout mice. *J. Neurosci.* 19:4907–4920.

Diamond I and Gordon A S (1997) Cellular and molecular neuroscience of alcoholism. *Physiol. Rev.* 77:1–20.

Dwyer D S and Bradley R J (2000) *Cell Mol. Life Sci.* 57:265–275.

Franks N P & Lieb W R (1984) *Nature* 310:599–601.

Franks N P and Lieb W R (1994) Molecular and cellular mechanisms of general anaesthesia. *Nature* 367:607–614.

Fransen E, Dhooge R, Vancamp G, Verhoye M, Sijbers J, Reyniers E, Soriano P, Kamiguchi H, Willemsen R, Koekkoek S K E, Dezeeuw C I, Dedeyn P P, Vanderlinden A, Lemmon V, Kooy R F and Willems P J (1998) L1 knockout mice show dilated ventricles, vermis hypoplasia and impaired exploration patterns. *Human Mol. Genet.* 7:999–1009.

Fransen E, Lemmon V, Vancamp G, Vits L, Coucke P and Willems P J (1995) CRASH syndrome—Clinical spectrum of corpus callosum hypoplasia, retardation, adducted thumbs, spastic paraparesis and hydrocephalus due to mutations in one single gene, L1 [Review]. *Eur. J. Hum. Genet.* 3:273–284.

Goldstein D B (1983) *Pharmacology of Alcohol.* Oxford, N.Y.

Harris R A (1999) Ethanol actions on multiple ion channels: which are important? *Alcohol Clin. Exp. Res.* 23:1563–1570.

Harris T, Shahidullah M, Ellingson J S and Covarrubias M (2000) General anaesthetic action at an internal protein site involving the S4-S5 cytoplasmic loop of a neuronal K(+) channel. *J. Biol. Chem.* 275:4928–4936.

Hodge C W, Mehmert K K, Kelley S P, McMahon T, Haywood A, Olive M F, Wang D, Sanchez-Perez A M and Messing R O (1999) Supersensitivity to allosteric GABA (A) receptor modulators and alcohol in mice lacking PKCepsilon. *Nature Neuroscience* 2:997–1002.

Hundle B, McMahon T, Dadgar J, Chen C H, Mochly-Rosen D and Messing R O (1997) An inhibitory fragment derived from protein kinase Cepsilon prevents enhancement of nerve growth factor responses by ethanol and phorbol esters. *J. Biol. Chem.* 272:15028–15035.

Kamiguchi H and Lemmon V (1998) A neuronal form of the cell adhesion molecule L1 contains a tyrosine-based signal required for sorting to the axonal growth cone. *J. Neurosci.* 18:3749–3756.

Lewohl J M, Wilson W R, Mayfield R D, Brozowski S J, Morrisett R A and Harris R A (1999) G-protein-coupled inwardly rectifying potassium channels are targets of alcohol action. *Nat. Neurosci.* 2:1084–1090.

Lovinger D M (1999) 5-HT3 receptors and the neural actions of alcohols: an increasingly exciting topic. *Neurochem. Int.* 35:125–130.

Lüthi A, Laurent J-P, Figurov A, Muller D and Schachner M (1994) Hippocampal long-term potentiation and neural cell adhesion molecules L1 and NCAM. *Nature* 372:777–779.

Mascia M P, Mihic S J, Valenzuela C F, Schofield P R and Harris R A (1996) A single amino acid determines differences in ethanol actions on strychnine-sensitive glycine receptors. *Mol. Pharmacol.* 50:402–406.

Mascia M P, Trudell J R and Harris R A (2000) Specific binding sites for alcohols and anesthetics on ligand-gated ion channels. *Proc. Natl. Acad. Sci. U.S.A.* 97:9305–9310.

Mascia M P, Wick M J, Martinez L D and Harris R A (1998) Enhancement of glycine receptor function by ethanol: role of phosphorylation. *Br. J. Pharmacol.* 125:263–270.

McCreery M J and Hunt W A (1978) Physico-chemical correlates of alcohol intoxication. *Neuropharmacol.* 17:451–461.

McKenzie D, Franks N P and Lieb W R (1995) Actions of general anaesthetics on a neuronal nicotinic acetylcholine receptor in isolated identified neurones of Lymnaea stagnalis. *Br. J. Pharmacol.* 115:275–282.

Mihic S J, Ye Q, Wick M J, Koltchine V V, Krasowski M D, Finn S E, Mascia M P, Valenzuela C F, Hanson K K, Greenblatt E P, Harris R A and Harrison N L (1997) Sites of alcohol and volatile anaesthetic action on GABA(A) and glycine receptors [see comments]. *Nature* 389:385–389.

Minami K, Gereau R Wt, Minami M, Heinemann S F and Harris R A (1998) Effects of ethanol and anesthetics on type 1 and 5 metabotropic glutamate receptors expressed in *Xenopus laevis* oocytes. *Mol. Pharmacol.* 53:148–156.

Miyakawa T, Yagi T, Kitazawa H, Yasuda M, Kawai N, Tsuboi K and Niki H (1997) Fyn-kinase as a determinant of ethanol sensitivity: relation to NMDA-receptor function [see comments]. *Science* 278:698–701.

Peoples R W, Li C and Weight F F (1996) *Ann. Rev. Pharmacol. Toxicol.* 36: 185–201.

Perides G, Hu G, Rueger D C and Charness M E (1993) *J. Biol. Chem.* 268:25197–25205.

Perides G, Safan R M, Downing L A and Charness M E (1994) *J. Biol. Chem.* 269:765–770.

Perides G, Safran R M, Rueger D C and Charness M E (1992) *Proc. Natl. Acad. Sci.* (USA) 89:10326–10330.

Ramanathan R, Wilkemeyer M F, Mittal B, Perides G and Charness M E (1996) Ethanol inhibits cell-cell adhesion mediated by human L1. *J. Cell Biol.* 133:381–390.

Rose S P (1995) Glycoproteins and memory formation. *Behav. Brain Res.* 66:73–78.

Sanna E, Dildy-Mayfield J E and Harris R A (1994) Ethanol inhibits the function of 5-hydroxytryptamine type 1c and muscarinic M1 G protein-linked receptors in *Xenopus oocytes* expressing brain mRNA: role of protein kinase C. *Mol. Pharmacol.* 45:1004–1012.

Slater S J, Cox K J, Lombardi J V, Ho C, Kelly M B, Rubin E and Stubbs C D (1993) Inhibition of protein kinase C by alcohols and anaesthetics. *Nature* 364:82–84.

Solem M, McMahon T and Messing R O (1997) Protein kinase A regulates regulates inhibition of N- and P/Q-type calcium channels by ethanol in PC12 cells. *J. Pharmacol. Exp. Ther.* 282:1487–1495.

Uyemura K, Asou H, Yazaki T and Takeda Y (1996) *Essays Biochem.* 31:37–48.

Vallejo Y, Hortsch M and Dubreuil R R (1997) *J. Biol. Chem.* 272:12244–7.

Wick M J, Mihic S J, Ueno S, Mascia M P, Trudell JR, Brozowski S J, Ye Q, Harrison N L and Harris R A (1998) Mutations of gamma-aminobutyric acid and glycine receptors change alcohol cutoff: Evidence for an alcohol receptor? *Proc. Natl. Acad. Sci. (U.S.A.)* 95:6504–6509.

Wilkemeyer M F and Charness M E (1998) Characterization of alcohol-sensitive and insensitive fibroblast cell lines expressing human L1. *J. Neurochem.* 71:2382–2391.

Wilkemeyer M F, Pajerski M and Charness M E (1999) Alcohol inhibition of cell adhesion in BMP-treated NG108-15 cells. *Alcohol Clin. Exp. Res.* 23:1711–1720.

Wilkemeyer M F, Sebastian A B, Smith S A and Charness M E (2000) Antagonists of alcohol inhibition of cell adhesion. *Proc. Natl. Acad. Sci. (U.S.A.)* 97:3690–3695.

Wong E V, Kenwrick S, Willems P and Lemmon V (1995) *Trends Neurosci.* 18:168–172.

Ye Q, Koltchine V V, Mihic S J, Mascia M P, Wick M J, Finn S E, Harrison N L and Harris R A (1998) Enhancement of glycine receptor function by ethanol is inversely correlated with molecular volume at position alpha267. *J. Biol. Chem.* 273:3314–3319.

Zhou Q L, Zhou Q and Forman S A (2000) The n-alcohol site in the nicotinic receptor pore is a hydrophobic patch. *Biochemistry* 39:14920–14926.

Zisch A H, Stallcup W B, Chong L D, Dahlinhuppe K, Voshol J, Schachner M and Pasquale E B (1997) Tyrosine phosphorylation of L1 family adhesion molecules—implication of the Eph Kinase Cek5. *J. Neurosci. Res.* 47:655–665.

What is claimed is:

1. A method of antagonizing alcohol inhibition effects on cell adhesion, comprising:

contacting a cell-adhesion molecule expressing cell with an effective amount of a compound; and wherein the compound comprises an alcohol selected from the group consisting of 3-pentanol, 2-pentanol, cyclopentanol, 4-methyl-1-pentanol, 2-methyl-2-pentanol, and 2,6-diisopropylphenol.

2. The method of claim 1, wherein:

said cell-adhesion molecule comprises L1 molecule.

3. The method of claim 1, wherein:

said cell-adhesion molecule expressing cell comprises a neural or fibroblast cell.

* * * * *

UNITED STATES PATENT AND TRADEMARK OFFICE
CERTIFICATE OF CORRECTION

PATENT NO. : 6,977,272 B2
APPLICATION NO. : 10/270551
DATED : December 20, 2005
INVENTOR(S) : Michael F. Wilkemeyer and Michael E. Charness It is certified that error appears in the above-identified patent and that said Letters Patent is hereby corrected as shown below:

Please insert the following paragraph at Column 1, before line 5:

--STATEMENT REGARDING FEDERALLY SPONSORED RESEARCH OR DEVELOPMENT

This invention was supported by grants AA011297 and AA009669 awarded by the National Institutes of Health. The government has certain rights to this invention.--

Signed and Sealed this

Third Day of March, 2009

JOHN DOLL
*Acting Director of the United States Patent and Trademark Office*